United States Patent
Chien et al.

(10) Patent No.: US 6,663,278 B1
(45) Date of Patent: Dec. 16, 2003

(54) METHOD FOR DETERMINING THE THERMAL PERFORMANCE OF A HEAT SINK

(75) Inventors: Heng Chieh Chien, Taipei (TW); Ming Hsi Tseng, Taipei (TW); Wen Wang Ke, Hsinchu (TW); Chih Yao Wang, Hsinchu (TW); Yi Shiau Chen, Yunlin (TW)

(73) Assignee: Industrial Technologies Research Institute, Hsin Chu (TW)

( * ) Notice: Subject to any disclaimer, the term of this patent is extended or adjusted under 35 U.S.C. 154(b) by 0 days.

(21) Appl. No.: 10/194,149

(22) Filed: Jul. 11, 2002

(51) Int. Cl.⁷ .......................... G01N 25/20; G01N 25/18
(52) U.S. Cl. .......................................... 374/43; 374/44
(58) Field of Search .............................. 374/43, 44, 57; 73/865.6

(56) References Cited

U.S. PATENT DOCUMENTS

| | | | |
|---|---|---|---|
| 3,266,290 A | * 8/1966 | Haacke | 374/44 |
| 4,324,285 A | * 4/1982 | Henderson | 165/11.1 |
| H000229 H | * 3/1987 | Phillips | 73/865.6 |
| 4,840,495 A | * 6/1989 | Bonnefoy | 374/43 |
| 5,318,361 A | * 6/1994 | Chase et al. | 374/57 |
| 2001/0030039 A1 | * 10/2001 | Copeland et al. | 165/104.26 |

FOREIGN PATENT DOCUMENTS

| | | | | |
|---|---|---|---|---|
| FR | 2592490 A1 | * 7/1987 | | 374/43 |
| JP | 55023477 A | * 2/1980 | | 374/44 |
| JP | 55147337 A | * 11/1980 | | 374/44 |
| JP | 62172248 A | * 7/1987 | | 374/44 |

* cited by examiner

Primary Examiner—Diego Gutierrez
Assistant Examiner—Mirellys Jagan
(74) Attorney, Agent, or Firm—Tung & Associates

(57) ABSTRACT

A method for determining the thermal resistance constant of a modular heat sink. The method can be carried out by first providing a heat capacity tank formed of a high thermal conductivity metal. A modular heat sink is then mounted on top of the heat capacity tank and heated together with the tank to a temperature of at least 40° C. The heating is then stopped and the heat sink/heat capacity tank is allowed to cool for at least 30 seconds before the temperature and the cooling time of the heat capacity tank is monitored and recorded. The function of dT/dt is then calculated. The amount of heat dissipated is then calculated from the equation of $Q = W \cdot C_p \cdot (dT/dt)$, while the thermal resistance constant is calculated by the equation of $R = (T - T_{amb})/Q$.

20 Claims, 3 Drawing Sheets

| THERMAL MODULE | INVENTION | | CONVENTIONAL | | % DIFFERENCE |
| --- | --- | --- | --- | --- | --- |
| | HEAT DISSIPATION CONSTANT | TEST TIME | HEAT DISSIPATION CONSTANT | TEST TIME | |
| #1 | 1.462 | 5 MIN | 1.447 | 30 MIN | 1.03% |
| #2 | 3.645 | 5 MIN | 3.54 | 60 MIN | 2.88% |
| #3 | 3.08 | 5 MIN | 2.96 | 60 MIN | 3.90% |
| #4 | 4.76 | 5 MIN | 4.515 | 75 MIN | 5.15% |
| #5 | 3.438 | 5 MIN | 3.383 | 60 MIN | 1.60% |
| #6 | 2.246 | 5 MIN | 2.1867 | 60 MIN | 2.64% |

THERMAL MODULE #1

THERMAL MODULE #2

THERMAL MODULE #3

THERMAL MODULE #4

THERMAL MODULE #5

THERMAL MODULE #6

METHOD FOR DETERMINING THE THERMAL PERFORMANCE OF A HEAT SINK

FIELD OF THE INVENTION

The present invention generally relates to a method for testing a semiconductor device, and more particularly, relates to a method for testing the thermal resistance efficiency of a heat sink attached to a semiconductor device.

BACKGROUND OF THE INVENTION

In modern semiconductor devices, the high density of the IC device (or the smaller chip size) requires that circuits to be placed on a chip close together. In order to maintain a reasonable service life of an IC device, the operating temperature of the device must be carefully controlled by providing adequate thermal resistance for the large amount of heat generated by the high density chip. Another development in modern IC devices which further requires improved thermal resistance is the increasing use of higher power consumption circuits. For instance, in a conventional 208-pin PQFP device, only 1 watt power dissipation is required. The power dissipation, which is closely related to the thermal resistance property, becomes more severe in a modern CPU chip which requires 30–50 watts power dissipation capability. The thermal resistance property of a conventional IC package must be improved in order to accommodate the more densely packaged and the higher power consumption IC devices.

A heat sink, normally fabricated of a high thermal conductivity material is used to fulfill the need for improving thermal resistance in IC packages. A heat sink is typically made of a material that has a high thermal conductivity, i.e., copper, aluminum, and their alloys. In order to efficiently dissipate heat, the heat sink should be in good thermal contact with a semiconductor die.

To improve the thermal resistance efficiency of an IC device, an external add-on heat sink can be fixed intimately to the device. This is shown in FIG. 1 for a conventional ceramic pin grid array package equipped with a modular (bolted-on) heat sink.

As shown in FIG. 1, the modular heat sink 10 is mechanically fastened to the ceramic pin grid array package 20 by two studs 22 and two nuts 12. The modular heat sink is of the fin type connected to the package 20 through a thermally conductive metal foil 14. An IC die 24 is attached to the bottom of the package 20 through thermally conductive adhesive coated on the IC die 24. A package lid 26 is further used to cover or to protect the IC die 24 when installed in the package 20. The package 20 is further equipped with a brazed-on heat slug 28 to further improve the thermal resistance of the package through the metal foil 14 and the modular heat sink 10.

The modular heat sink 10 is frequently designed with one or two holes 16 to accommodate studs 22 and nuts 12 which are used to fasten the modular heat sink 10 to the package 20. To further improve the heat conductance, a thermal interface such as grease, graphite or metal foil 14 is used at the package/slug and heat sink interface to eliminate air gaps and therefore improve the thermal path.

In order to ensure the effectiveness in thermal resistance for the various designs of heat sinks, a reliable test method must be provided to measure such efficiency. The test method must also be able to be conducted in a short time period in order to maintain the overall efficiency of the IC fabrication process. Conventionally, the thermal resistance efficiency of a heat sink is determined by mounting a modular heat sink on top of a heating element and then heated. After the temperature of the modular heat sink reached a preset value and stabilized, the temperature of the heating device is measured. The amount of heat generated by the heating device is then divided by the differential temperature between the heating device and the surrounding environment to calculate the thermal performance (thermal resistance) constant of the modular heat sink. To obtain a stable, reliable, reading, the temperature must be stabilized which requires a total test time for the modular heat sink of about 30 minutes or longer. The lengthy test procedure requires substantial manpower and cost which becomes prohibitive when 100% reliability test is required for future high efficiency IC devices.

It is therefore an object of the present invention to provide a method for determining the thermal resistance constant of a heat sink without the drawbacks or shortcomings of the conventional methods.

It is another object of the present invention to provide a method for determining the thermal resistance constant of a heat sink which can be carried out in a short testing time of about 5 min.

It is a further object of the present invention to provide a method for determining the thermal resistance constant of a heat sink which can be used to obtain data that are within 5% of data obtained by conventional methods.

It is another further object of the present invention to provide a method for determining the thermal resistance constant of a heat sink by mounting the heat sink on top of a heat capacity tank formed of a high thermal conductivity metal.

It is still another object of the present invention to provide a method for determining the thermal resistance constant of a heat sink wherein the heat sink may be cooled with or without a forced air cooling system.

SUMMARY OF THE INVENTION

In accordance with the present invention, a method for determining the thermal resistance constant of a heat sink is provided.

In a preferred embodiment, a method for determining the thermal resistance constant of a heat sink can be carried out by the operating steps of providing a heat capacity tank fabricated of a metal; mounting a heat sink on top of the heat capacity tank; heating the heat capacity tank and the heat sink to a temperature of at least 40° C.; stopping the heating step and cooling for at least 30 seconds; monitoring temperature and cooling time of the heat capacity tank for a preset length of time and calculating dT/dt; calculating the amount of heat dissipated from the equation of $Q = W \cdot C_p \cdot (dT/dt)$ wherein W and $C_p$ are the weight and the heat capacity of the heat capacity tank, respectively; and calculating the thermal resistance constant from the equation of $R = (T - T_{amb})/Q$ wherein T and $T_{amb}$ are the temperature of the heat capacity tank and ambient temperature, respectively.

The method for determining the thermal resistance constant of a heat sink may further include the step of stopping the heating step and turning on a forced-air cooling device for a time period of at least 1 min. prior to the monitoring step. The heat capacity tank may be formed of a metal having a thermal conductivity of at least that of Zn, or the heat capacity tank may be formed of a metal selected of the group consisting of Cu, Al, Au and Zn. The heat capacity tank may be formed of a metal that has a heat capacity not higher than that of Zn. The preset length of time for the monitoring step is at least 3 min., or between about 3 min. and about 10 min. The method may further include the step of heating the heat capacity tank and the heat sink to a temperature of at least 70° C. or to a temperature of at least 90° C. The method may further include the step of mounting a heater in the heat capacity tank, or mounting an electric heater in the heat capacity tank, or flowing an electrical current to the heater in the heat capacity tank.

The present invention is further directed to a method for determining the thermal resistance constant of a thermal module which may be carried out by the steps of providing a heat capacity tank fabricated of a metal; mounting a thermal module on top of the heat capacity tank; heating the heat capacity tank and the thermal module to a temperature of at least 40° C.; stopping the heating step and cooling for at least 30 seconds; monitoring temperature and cooling time of the heat capacity tank for a preset length of time and calculating dT/dt; calculating the amount of heat dissipated from the equation $Q=W \cdot C_p \cdot (dT/dt)$ wherein W and $C_p$ are the weight and heat capacity of the heat capacity tank, respectively; and calculating the thermal resistance constant from the equation of $R=(T-T_{amb})/Q$ wherein T and $T_{amb}$ are the temperature of the heat capacity tank and the ambient temperature, respectively.

The method for determining the thermal resistance constant of a thermal module may further include the step of stopping the heating step and turning on a forced-air cooling device for a time period of at least 1 min. prior to the monitoring step. The heat capacity tank may be formed of a metal that has a conductivity of at least that of Zn, or formed of a metal selected from the group consisting of Cu, Al, Au and Zn. The method may further include the step of providing the heat capacity tank including heating plates for heating the heat capacity tank, at least one thermal couple for measuring temperature of the heat capacity tank, and a thermal insulating blanket surrounding the heat capacity tank. The method may further include the step of providing the thermal module in a fin-shaped heat sink, or in a pin-shaped heat sink. The method may further include the step of mounting a thermal module on top of the heat capacity tank with a thermal conductive layer therein-between.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENTS

The present invention discloses a method for determining the thermal resistance constant of a heat sink, or of a modular heat sink that can be mounted on top of an IC package.

The method can be carried out by first forming a heat capacity tank of a metal that has high thermal conductivity and high heat capacity. The modular heat sink is then, mounted on top of the heat capacity tank and heated by a heating device built inside the heat capacity tank to a preset temperature, such as a temperature of 40° C., or 70° C., or 90° C. After the temperature reaches the preset temperature, the heating is stopped and the heat capacity tank is left to cool for at least 30 seconds. For instance, for a modular heat sink that is equipped with a forced-air cooling device, i.e., a fan, the heat capacity tank is cooled by the fan for approximately 1 min. The temperature and the cooling time of the heat capacity tank is then monitored and recorded for a present length of time, i.e., for 3 min., or for a time period of less than 5 min. The temperature change as a function of the cooling time, i.e., dT/dt, is then calculated from the temperature/time curve.

The amount of heat dissipated by the modular heat sink can be calculated by the equation of $$Q=W \cdot C_p \cdot (dT/dt)$$

Wherein W and $C_p$ are the weight and the heat capacity of the heat capacity tank, respectively.

The thermal resistance constant of the modular heat sink can then be calculated from the equation $$R=(T-T_{amb})/Q$$

Wherein T and $T_{amb}$ are the temperature of the heat capacity tank and the temperature of the ambient, respectively.

The present invention method can be conducted in a very short period of time, i.e., in less than 5 min. when compared to the test time required by the conventional method of approximately 30 minutes. The present invention test method does not require the temperature of a heat capacity tank to be stabilized by monitoring the temperature change with cooling time, and therefore, the test time can be greatly reduced. Moreover, in the conventional method, the total amount of heat dissipated by the modular heat sink is fixed contrary to the present invention method, wherein the total amount of heat dissipated changes with temperature. The lower the temperature, the smaller the total amount of heat dissipated.

Figure 1:
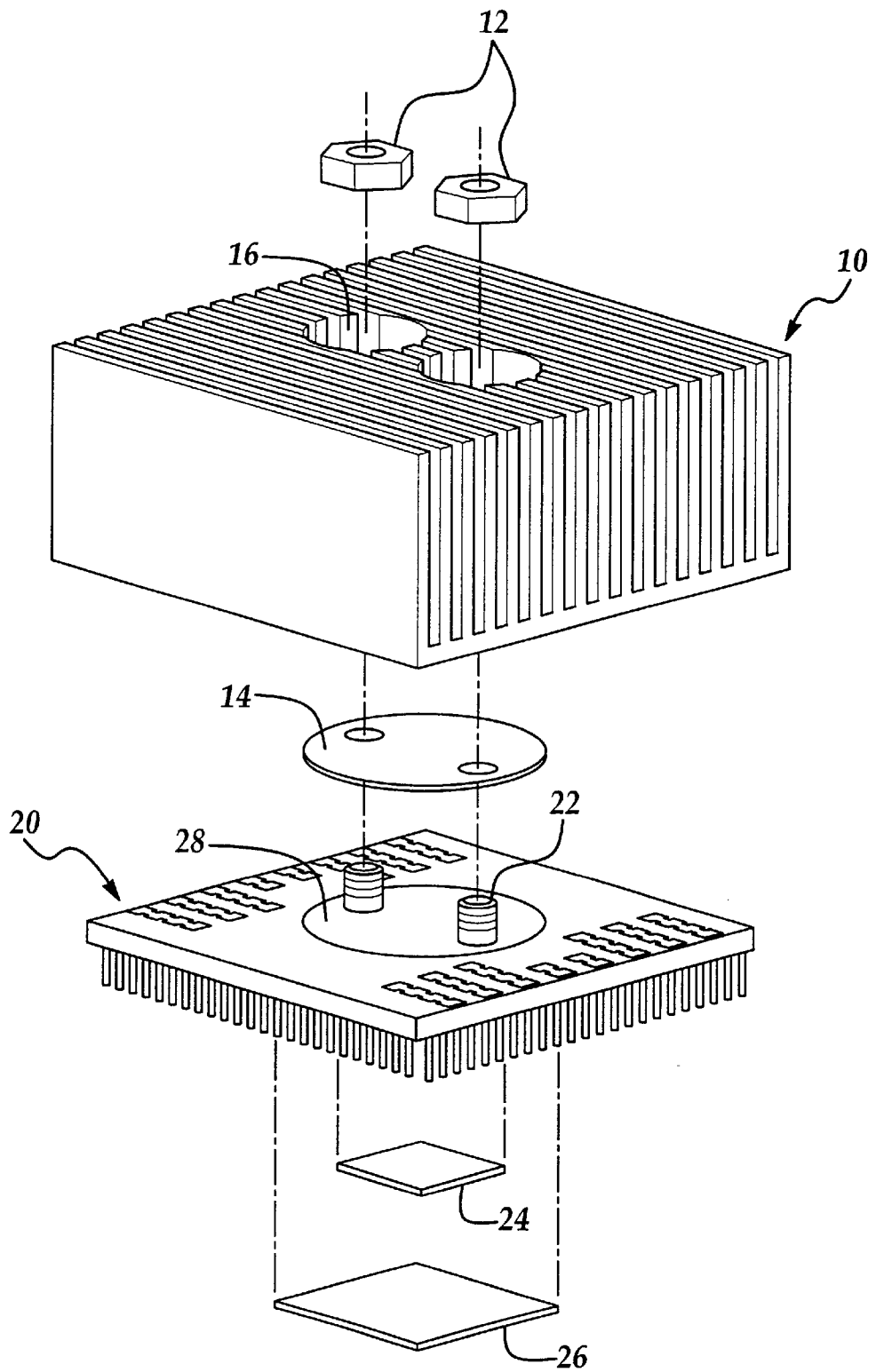
FIG. 1 is a perspective view of a conventional set up of a ceramic pin grid array device with a modular heat sink mounted on top.
Figures 2, 4:
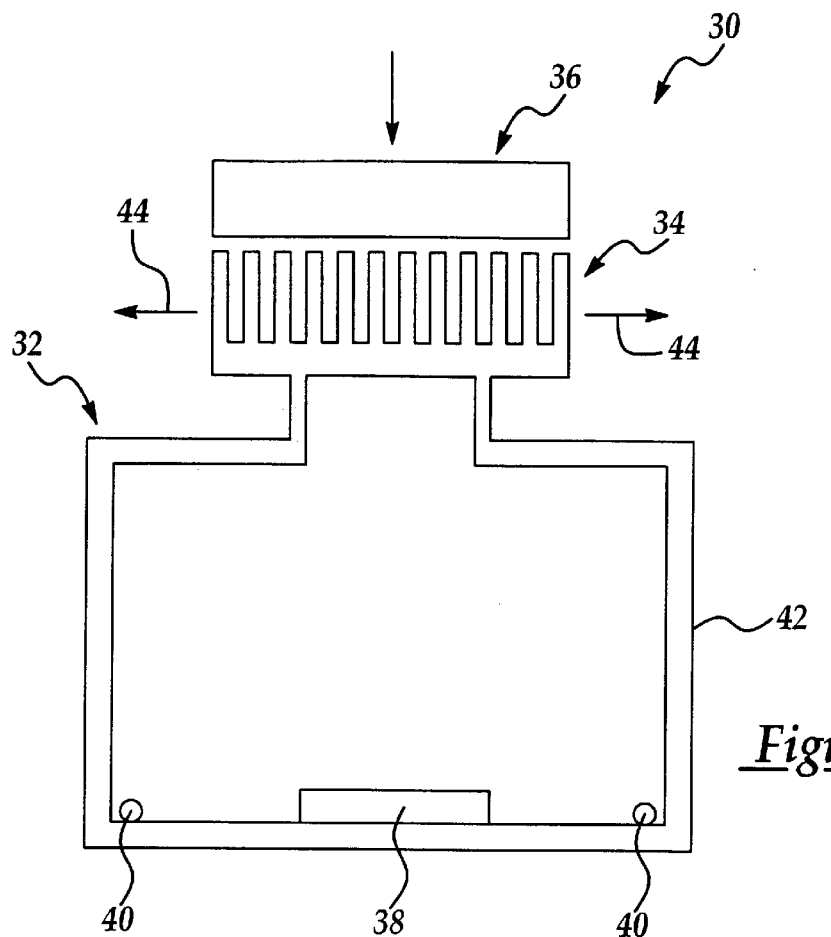
FIG. 2 is a cross-sectional view of the present invention test apparatus.
FIG. 4 is a table illustrating the efficiency of the present invention test method when compared to the conventional test method.

A set-up 30 for carrying out the present invention novel method is shown in FIG. 2. The set-up 30 includes a thermal capacity tank 32, a modular heat sink (or a thermal module) 34, a forced air cooling device 36. The heat capacity tank 32 is further equipped with a heating device 38 and at least one thermocouple 40. The thermal capacity tank 32 is further surrounded by a thermal insulating blanket 42 to maintain the temperature of the thermal capacity tank 32. Heat contained in the thermal capacity tank 32 is conducted to the modular heat sink 34 and dissipated as heat 44 shown in FIG. 2. The forced air cooling device 36, i.e., an electric fan, facilitates the thermal resistance from the modular heat sink 34.

The heat capacity tank 32 includes at least one thermocouple 40, a heating device 38 (an electric heater) and the thermal insulation blanket 42. The heater 38 can be either attached to the outer surface of the heat capacity tank 32, or can be inserted into the interior cavity of the heat capacity tank 32. The thermal insulating blanket 42 used can be formed of any suitable thermal insulating material for reducing thermal resistance to the surrounding air. The heat capacity tank 32 can be formed of a metal that has high heat conductance and low heat capacity to allow the tank to achieve more uniform temperature distribution during the thermal resistance cycle. Commonly known high thermal conductivity metals such as Cu, Al, Au, Zn, etc., can be used to form the present invention heat capacity tank 32. The shape of the heat capacity tank 32, as shown in FIG. 2, is formed in a cube. However, any other suitable shape may also be used without significantly affecting the efficiency of the present invention method.

A typical curve fitting equation is used in a computer software for calculating dT/dt from data obtained on the heat capacity tank 32.

Figure 3:
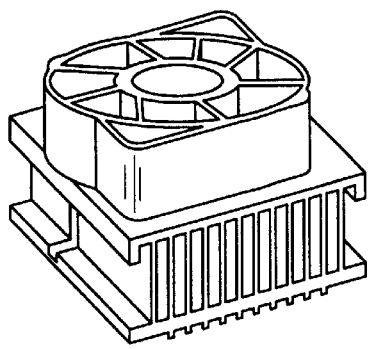
FIG. 3 is a perspective view of the various thermal modules tested by the present invention method.
Figure 3:
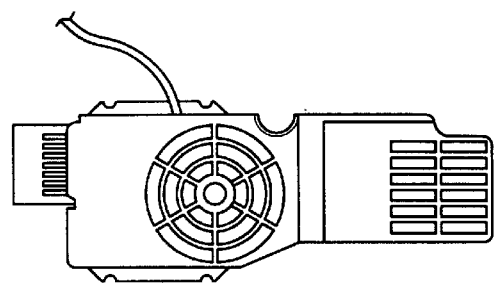
Figure 3:
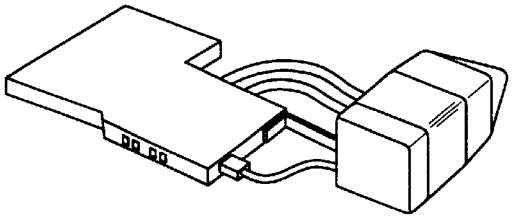
Figure 3:
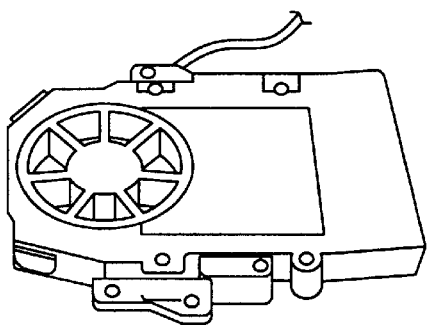
Figure 3:
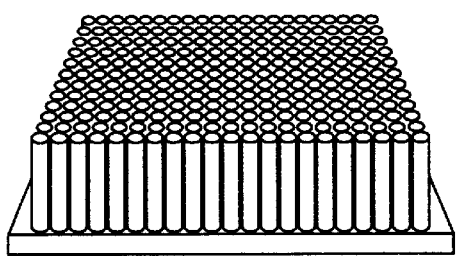
Figure 3:
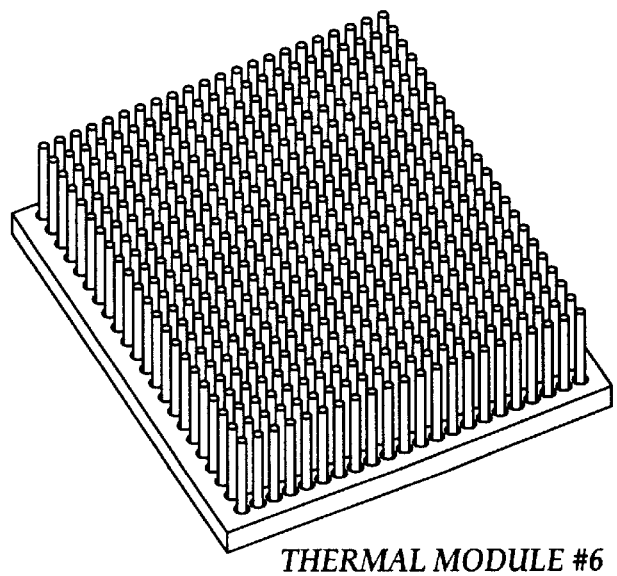

The present invention novel method has been tested on various modular heat sinks, shown in FIG. 3, to verify the efficiency of the method. For instance, thermal modules 1, 2, 3 and 4, shown in FIG. 3, are equipped with forced air cooling devices, i.e., an electric fan. Thermal modules 5 and 6, shown in FIG. 3, are formed in fins and pins without the fan attachment.

Data obtained on the various thermal module arrangements of FIG. 3 are shown in FIG. 4. It is seen that by utilizing the present invention method, the test time is reduced to 5 min. from the test time of between 30 and 75 min. required for the conventional methods. Furthermore, the thermal resistance constants obtained by the present invention method deviates from those obtained by the conventional methods by less than 5%, which confirms the accuracy of the present invention method.

The present invention method for determining the thermal resistance constant of a heat sink, or of a modular heat sink, has therefore been amply described in the above description and in the appended drawings of FIGS. 2–4.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows.

What is claimed is:

1. A method for determining the thermal resistance constant of a thermal module comprising the steps of:

providing a heat capacity tank fabricated of a metal;

mounting a thermal module on top of said heat capacity tank;

heating said heat capacity tank and said thermal module to a temperature of at least 40° C.;

stopping said heating step and cooling for at least 30 sec.;

monitoring temperature and cooling time of said heat capacity tank for a preset length of time and calculating dT/dt;

calculating the amount of heat dissipated by the module from the equation $$Q = W \cdot C_p \cdot (dT/dt)$$

wherein W and $C_p$ are the weight and the heat capacity of the heat capacity tank, respectively; and calculating the thermal resistance constant of the module from the equation $$R = (T - T_{amb})/Q$$

wherein T and $T_{amb}$ are the temperature of the heat capacity tank and the ambient temperature, respectively.

2. A method for determining the thermal resistance constant of a thermal module according to claim 1, further comprising the step of stopping said heating step and turning on a forced-air cooling device for a time period of at least 1 min. prior to said monitoring step.

3. A method for determining the thermal resistance constant of a thermal module according to claim 1, wherein said heat capacity tank is formed of a metal having a thermal conductivity of at least that of Zn.

4. A method for determining the thermal resistance constant of a thermal module according to claim 1, wherein said heat capacity tank is formed of a metal selected from the group consisting of Cu, Al, Au and Zn.

5. A method for determining the thermal resistance constant of a thermal module according to claim 1, further comprising the step of providing said heat capacity tank with:

heating plates for heating said heat capacity tank;

at least one thermocouple for measuring temperature of said heat capacity tank; and a thermal insulating blanket surrounding said heat capacity tank.

6. A method for determining the thermal resistance constant of a thermal module according to claim 1, further comprising the step of providing said thermal module as a fin-shaped heat sink.

7. A method for determining the thermal resistance constant of a thermal module according to claim 1, further comprising the step of providing said thermal module as a pin-shaped heat sink.

8. A method for determining the thermal resistance constant of a thermal module according to claim 1, wherein the thermal module is mounted on top of said heat capacity tank with a thermal conductive layer therein-between.

9. A method for determining the thermal resistance constant of a heat sink comprising the steps of:

providing a heat capacity tank fabricated of a metal;

mounting a heat sink on top of said heat capacity tank;

heating said heat capacity tank and said heat sink to a temperature of at least 40° C.;

stopping said heating step and cooling for at least 30 sec.;

monitoring temperature and cooling time of said heat capacity tank for a preset length of time and calculating dT/dt;

calculating the amount of heat dissipated by the heat sink from the equation $$Q = W \cdot C_p \cdot (dT/dt)$$

wherein W and $C_p$ are the weight and the heat capacity of the tank, respectively; and calculating the thermal resistance constant of the heat sink from the equation $$R = (T - T_{amb})/Q$$

wherein T and $T_{amb}$ are the temperature of the heat capacity tank and the ambient temperature, respectively.

10. A method for determining the thermal resistance constant of a heat sink according to claim 9, further comprising the step of stopping said heating step and turning on a forced-air cooling device for a time period of at least 1 min. prior to said monitoring step.

11. A method for determining the thermal resistance constant of a heat sink according to claim 9, wherein said heat capacity tank is formed of a metal having a thermal conductivity of at least that of Zn.

12. A method for determining the thermal resistance constant of a heat sink according to claim 9, wherein said heat capacity tank is formed of a metal selected from the group consisting of Cu, Al, Au and Zn.

13. A method for determining the thermal resistance constant of a heat sink according to claim 9, wherein said heat capacity tank is formed of a metal having a heat capacity not higher than that of Zn.

14. A method for determining the thermal resistance constant of a heat sink according to claim 9, wherein said preset length of time for said monitoring step is at least 3 min.

15. A method for determining the thermal resistance constant of a heat sink according to claim 9, wherein said preset length of time for said monitoring step is between about 3 min and about 10 min.

16. A method for determining the thermal resistance constant of a heat sink according to claim 9, further comprising the step of heating said heat capacity tank and said heat sink to a temperature of at least 70° C.

17. A method for determining the thermal resistance constant of a heat sink according to claim 9, further comprising the step of heating said heat capacity tank and said heat sink to a temperature of at least 90° C.

18. A method for determining the thermal resistance constant of a heat sink according to claim 9, further comprising the step of mounting a heater in said heat capacity tank.

19. A method for determining the thermal resistance constant of a heat sink according to claim 9, further comprising the step of mounting an electric heater in said heat capacity tank.

20. A method for determining the thermal resistance constant of a heat sink according to claim 9, further comprising the step of flowing an electrical current to said heater in said heat capacity tank.

* * * * *